United States Patent
Sommerset

(10) Patent No.: US 11,903,688 B2
(45) Date of Patent: Feb. 20, 2024

(54) VASCULAR FLOW DIAGNOSTIC SYSTEM

(71) Applicant: MOONRISE MEDICAL INC., Oakville (CA)

(72) Inventor: Jill Sommerset, Parkdale, OR (US)

(73) Assignee: MOONRISE MEDICAL INC., Oakville (CA)

( * ) Notice: Subject to any disclaimer, the term of this patent is extended or adjusted under 35 U.S.C. 154(b) by 387 days.

(21) Appl. No.: 16/785,398

(22) Filed: Feb. 7, 2020

(65) Prior Publication Data

US 2020/0288993 A1 Sep. 17, 2020

Related U.S. Application Data

(63) Continuation of application No. PCT/US2018/053700, filed on Oct. 1, 2018.

(60) Provisional application No. 62/566,760, filed on Oct. 2, 2017.

(51) Int. Cl.
*A61B 5/0285* (2006.01)
*A61B 5/00* (2006.01)

(52) U.S. Cl.
CPC .......... *A61B 5/0285* (2013.01); *A61B 5/6825* (2013.01); *A61B 5/6829* (2013.01); *A61B 5/7253* (2013.01); *A61B 2562/04* (2013.01)

(58) Field of Classification Search
None
See application file for complete search history.

(56) References Cited

U.S. PATENT DOCUMENTS

| 4,432,374 A | 2/1984 | Osanai | |
| 5,868,676 A * | 2/1999 | McCabe | A61B 8/463 73/861.25 |
| 2002/0049384 A1 * | 4/2002 | Davidson | A61B 8/06 600/455 |
| 2002/0091320 A1 | 7/2002 | Crutchfield et al. | |
| 2010/0016733 A1 * | 1/2010 | Smith | A61B 5/0295 600/483 |
| 2011/0137210 A1 * | 6/2011 | Johnson | A61B 7/04 600/586 |
| 2012/0095332 A1 * | 4/2012 | Nitta | A61B 8/4483 600/437 |
| 2014/0058267 A1 * | 2/2014 | Kessler | A61B 8/06 600/454 |
| 2014/0249431 A1 | 9/2014 | Banet et al. | |

(Continued)

FOREIGN PATENT DOCUMENTS

DE 4214263 A1 11/1993
EP 3393365 * 12/2016 .............. A61B 8/06

OTHER PUBLICATIONS

Handa, Nobuo, et al. "Efficacy of echo-Doppler examination for the evaluation of renovascular disease." Ultrasound in medicine & biology 14.1 (1988): 1-5. (Year: 1988).*

(Continued)

*Primary Examiner* — Nathan J Jenness
*Assistant Examiner* — Jairo H Portillo
(74) *Attorney, Agent, or Firm* — HILL & SCHUMACHER

(57) ABSTRACT

A diagnostic system includes one or more blood flow sensors adapted to contact but not penetrate the skin of the pedal arch and aligned with blood vessels of the pedal arch. Readings from the blood flow sensors are transformed into blood flow acceleration times, and the blood flow acceleration times are used to identify a blood flow pathology.

8 Claims, 9 Drawing Sheets

(56) References Cited

U.S. PATENT DOCUMENTS

| | | | |
|---|---|---|---|
| 2015/0073271 A1* | 3/2015 | Lee .................... | A61B 5/02007 |
| | | | 600/475 |
| 2015/0359457 A1 | 12/2015 | Blumenthal et al. | |
| 2016/0058301 A1* | 3/2016 | Shusterman ........... | A61B 5/055 |
| | | | 600/301 |
| 2017/0251929 A1 | 9/2017 | Barodka | |
| 2017/0296807 A1* | 10/2017 | Brown ................. | A61N 1/0529 |
| 2019/0076034 A1* | 3/2019 | Mori ................. | A61B 5/02108 |

OTHER PUBLICATIONS

International Preliminary Report on Patentability for PCT Application PCT/US2018/053700, dated Apr. 7, 2020.
International Search Report for PCT Application PCT/US2018/053700, dated Dec. 17, 2018.
Written Opinion of the ISA for PCT Application PCT/US2018/053700, dated Dec. 17, 2018.

\* cited by examiner

|  | Normal | Mild Claudication | Severe Claudication | CLI – rest pain, tissue loss |
|---|---|---|---|---|
|  | 0-120 | 121-180 | 181-224 | >225 |
| ABI | 0.9-1.2 | 0.89-0.69 | 0.68-0.40 | 0.39-0.00 |
| TBI | >0.70 | >0.70 | 0.69-0.50 | 0.49-0.00 |

TABLE 1

FIG. 9

VASCULAR FLOW DIAGNOSTIC SYSTEM

CROSS-REFERENCE TO RELATED APPLICATIONS

This application claims priority and benefit as a Continuation application under 35 U.S.C. 111(a) to international application serial no. PCT/US18/53700, filed on Oct. 1, 2018, titled "VASCULAR FLOW DIAGNOSTIC SYSTEM", which claims priority to US application serial no. 62/566,760, filed on Oct. 2, 2017, each of which is incorporated by reference herein in their entirety.

BACKGROUND

Peripheral arterial disease (PAD) is a serious problem, affects at least 12 million people in the US. PAD is found most commonly in people over age 50 with a history of smoking, diabetes, high blood pressure or heart disease. PAD occurs when arteries in the legs become narrowed or blocked (occluded) by plaque build-up, reducing blood flow to the limbs. PAD can lead to interventions including amputation if left untreated.

With technological advances in vascular interventions and tools (wires and catheters and devices), advances in ultrasound detail, and the exponential rise in critical limb ischemia (CLI) the treatment of amputation prevention is being spotlighted across the country. The current practice to track if a patient has critical limb ischemia is perform (blood pressures) ankle-brachial indices (diagnostic technique 100 of FIG. 1 and diagnostic technique 200 of FIG. 2) and toe-brachial indices (diagnostic technique 300 of FIG. 3).

In a typical ABI approach (FIG. 1), the ABI value is determined by taking the higher pressure of the two arteries at the ankle, divided by the brachial arterial systolic pressure. In In a typical ABI approach (FIG. 1), the ABI value is determined by taking the higher pressure of the two arteries at the ankle, divided by the brachial arterial systolic pressure. In calculating the ABI, the higher of the two brachial systolic pressure measurements is used. Ranges are then consulted to determine a diagnosis, for example:

1.2 or greater—Medial Wall Calcification (Diabetes)
0.90-1.2 Normal
0.79-0.89—Mild Arterial Disease
0.50-0.78—Moderate Arterial Disease
0.49 or less—Severe Arterial Disease—Critical limb ischemia In a typical TBI approach (FIG. 2), the TBI value is determined by taking the pressure of the great toe, divided by the brachial arterial systolic pressure. Ranges are then consulted to determine a diagnosis, for example:

Normal—0.70 or greater
Abnormal—0.70 or less

These methods are widely known for not producing reliable diagnoses, especially in the case of diabetes where the measurements are very often erroneous.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

FIG. 9 illustrates a Table 900 in accordance with one embodiment.

DETAILED DESCRIPTION

Figure 1:
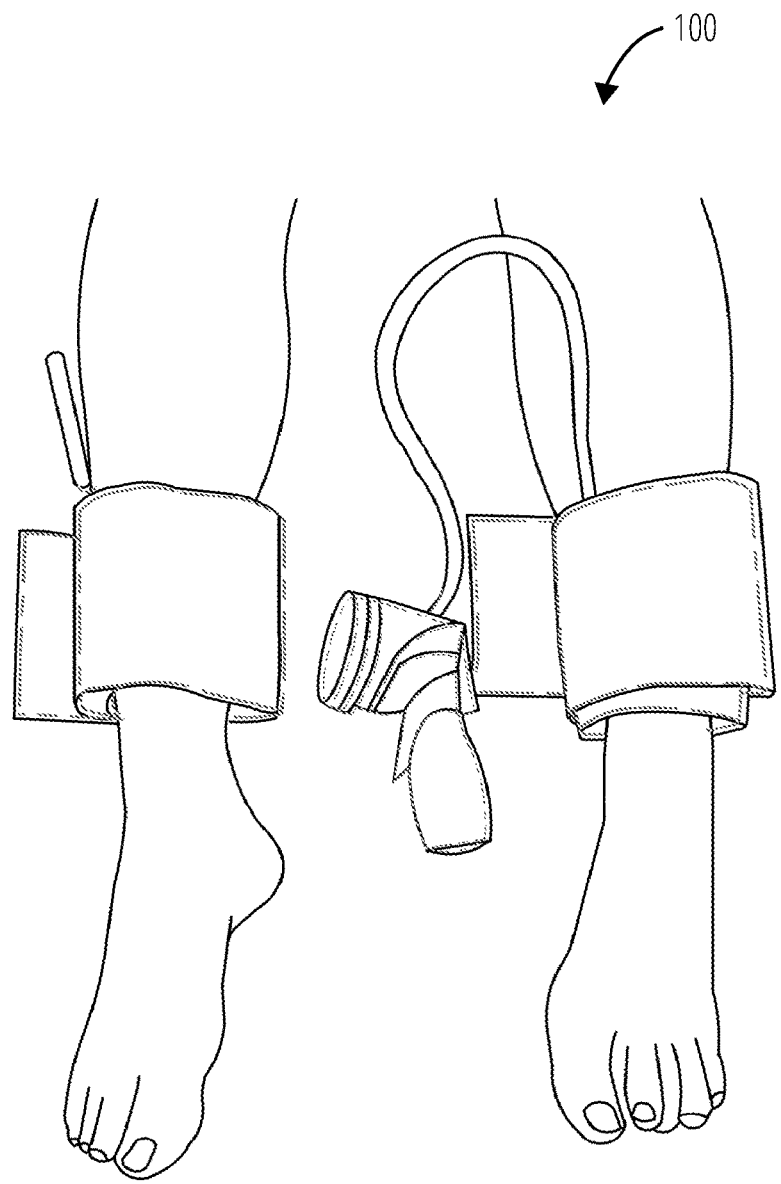
FIG. 1 illustrates a conventional diagnostic technique 100 for ankle brachial index (ABI) measurement.
Figure 2:
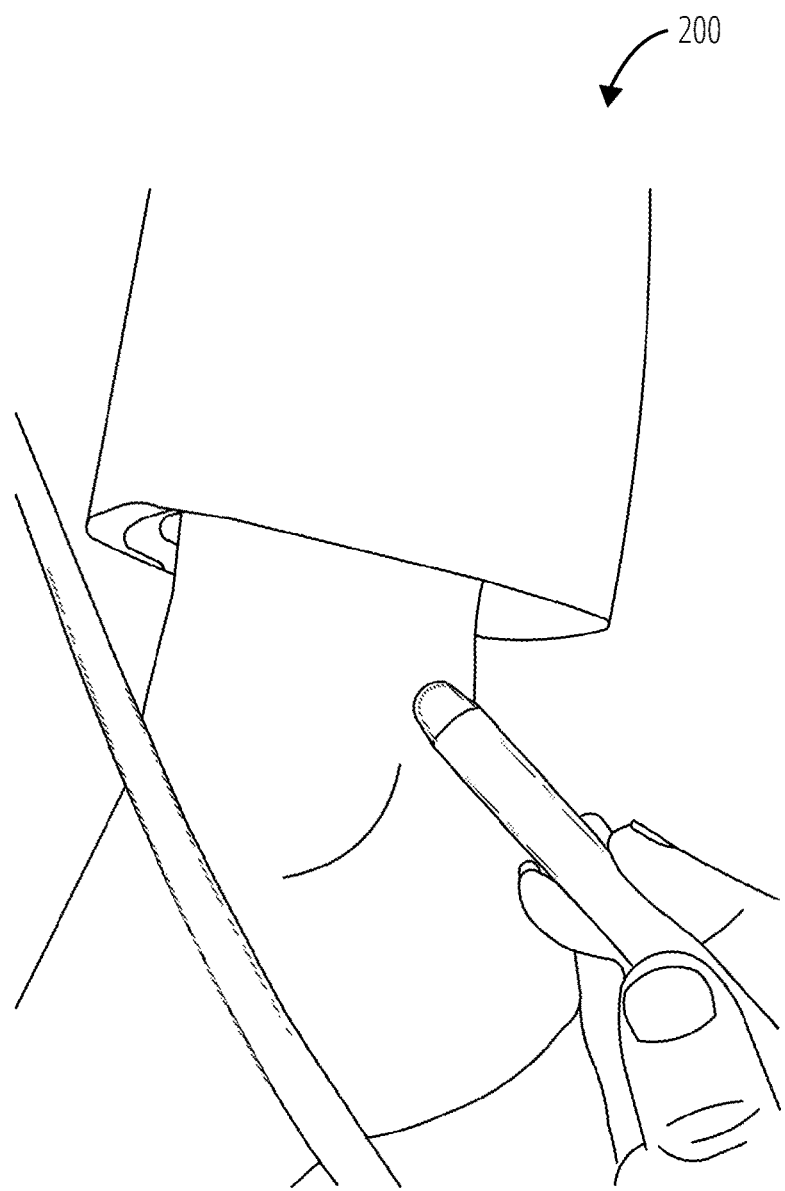
FIG. 2 illustrates a diagnostic technique 200 in accordance with one embodiment.
Figure 3:
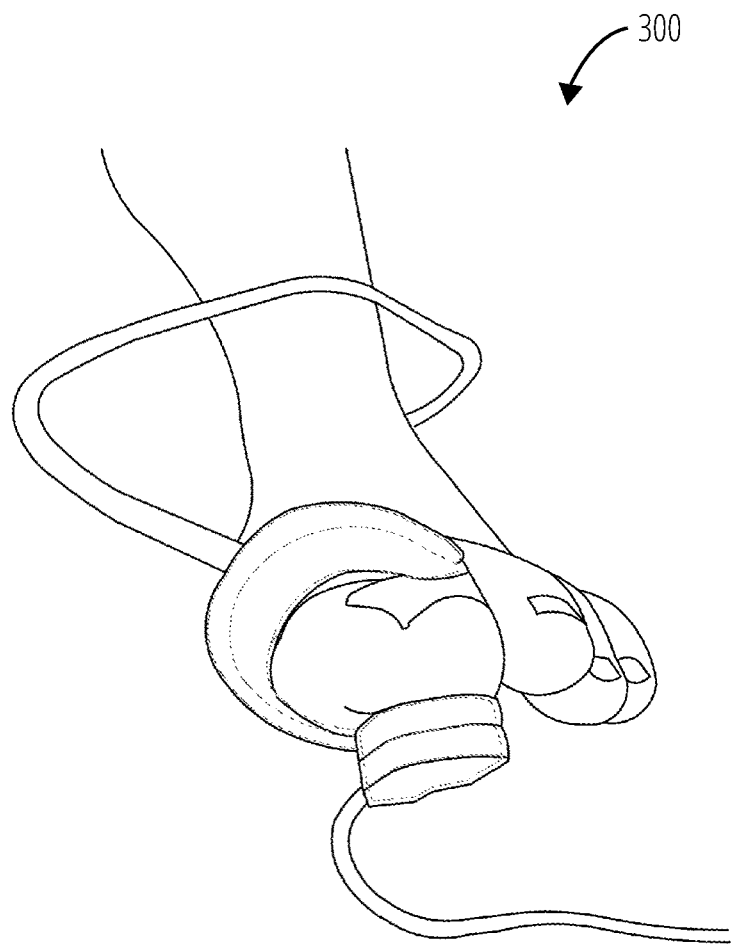
FIG. 3 illustrates a diagnostic technique 300 for toe brachial index (TBI).
Figure 4:
FIG. 4 illustrates an example of the pedal arch 400.

The pedal arch 400 in the foot (FIG. 4) provides an alternative diagnostic area for PAD, and an alternative approach to conventional ABI and TBI approaches that measure blood pressures. Disclosed herein are devices and procedures to utilize correlation between blood flow acceleration time in the pedal/plantar arteries and pathologies involving occluded blood vessels. Such techniques may be employed, for example, to demonstrate if enough blood flow is getting to the foot to heal a wound to prevent amputation.

Vascular specialists currently do not utilize reliable tools to accurately measure the amount of blood flow the foot. When a patient is in the operating room, there is no clear way for a physician to conclusively determine that enough blood flow is restored to the foot.

Figure 5:
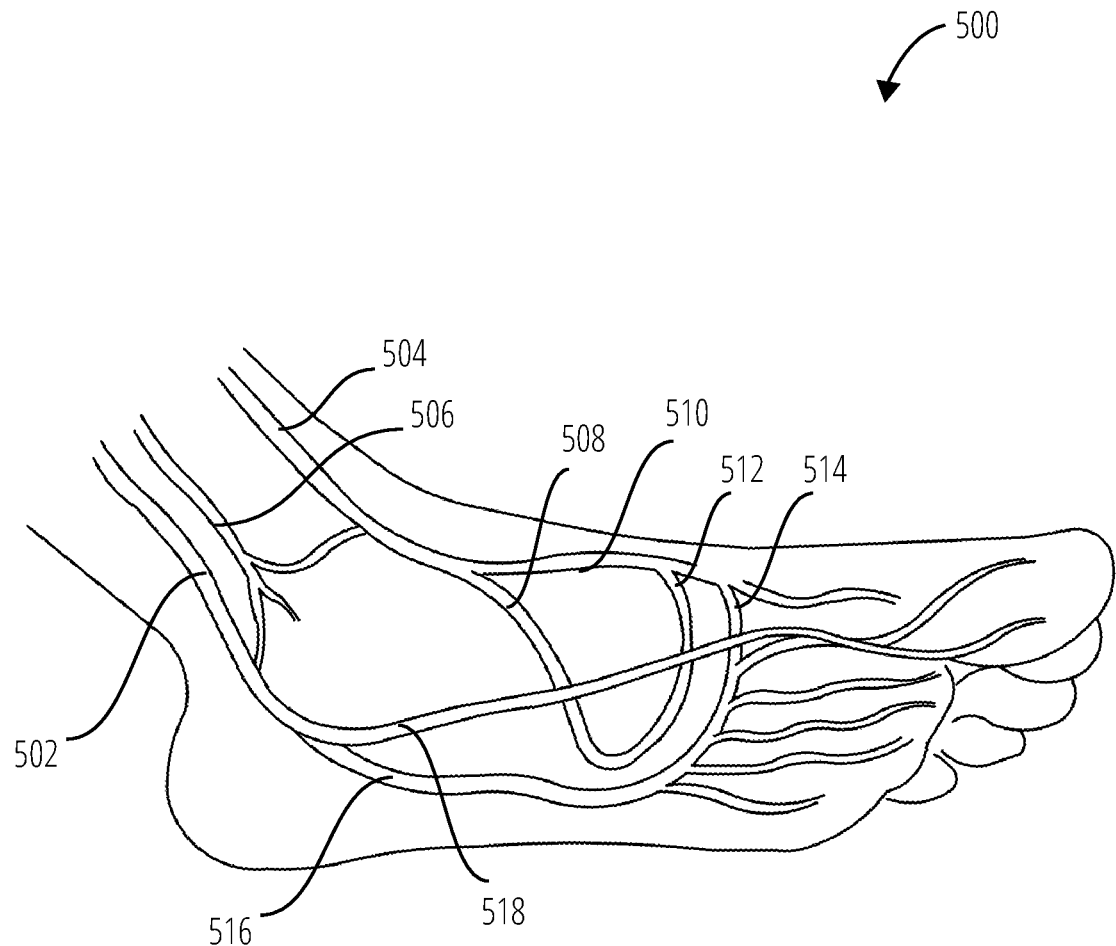
FIG. 5 illustrates blood vessels in the human foot 500 in accordance with one embodiment.

Referring to FIG. 5, the blood vessels in the human foot 500 include a posterior tibial artery 502, an anterior tibial artery 504, a peroneal artery 506, a lateral tarsal artery 508, a dorsalis pedis artery 510, an arcuate artery 512, a deep plantar artery 514, a lateral plantar artery 516, and a medial plantar artery 518.

Figure 6:
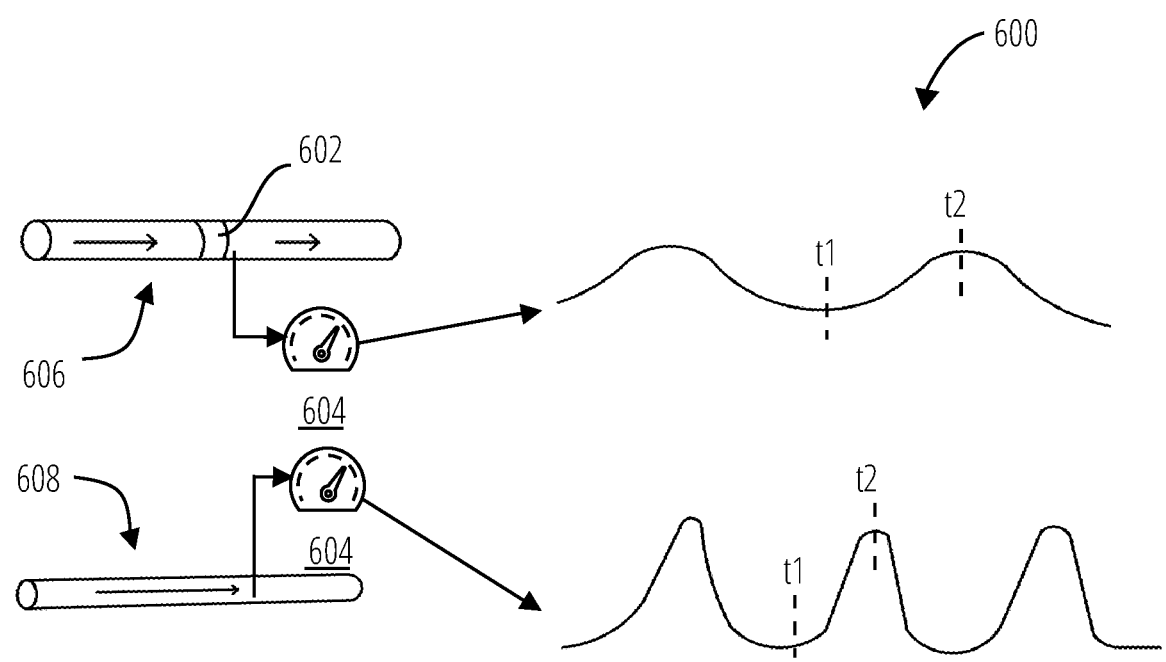
FIG. 6 illustrates blood flow acceleration measurement system 600 in accordance with one embodiment.

FIG. 6 illustrates blood flow acceleration measurement system 600 in accordance with one embodiment. The sensors 604 measures a time interval between a diastolic pressure (t1) and a systolic pressure (t2), or vice versa. An acceleration time for blood in the measured blood vessel may be computed from the difference of t2-t1 (or vice versa).

For an un-occluded blood vessel 608, the interval t2-t1 will typically be less than 100 milliseconds. For an occluded blood vessel 606 including an occlusion 602, the interval t2-t1 will typically exceed 225 milliseconds. See Table 900 in FIG. 9.

The sensors 604 may be utilized to measure the plantar acceleration time in the operating room, so that vascular specialists have reliable data to see real time physiologic feedback in the amount of blood flow the distal end point, the foot.

Slow acceleration time predicts low arterial blood supply areas for wound healing. Options for one or more sensors 604 to measure the acceleration time include continuous wave doppler and infra-red sensors. Photoplethysmography (PPG) is a simple and low-cost optical technique for the sensors 604 that can be used to detect blood volume changes in the microvascular bed of tissue. It may be deployed non-invasively to make measurements at the skin surface. Duplex ultrasound imaging is another sensor technology that may be utilized.

Figure 7:
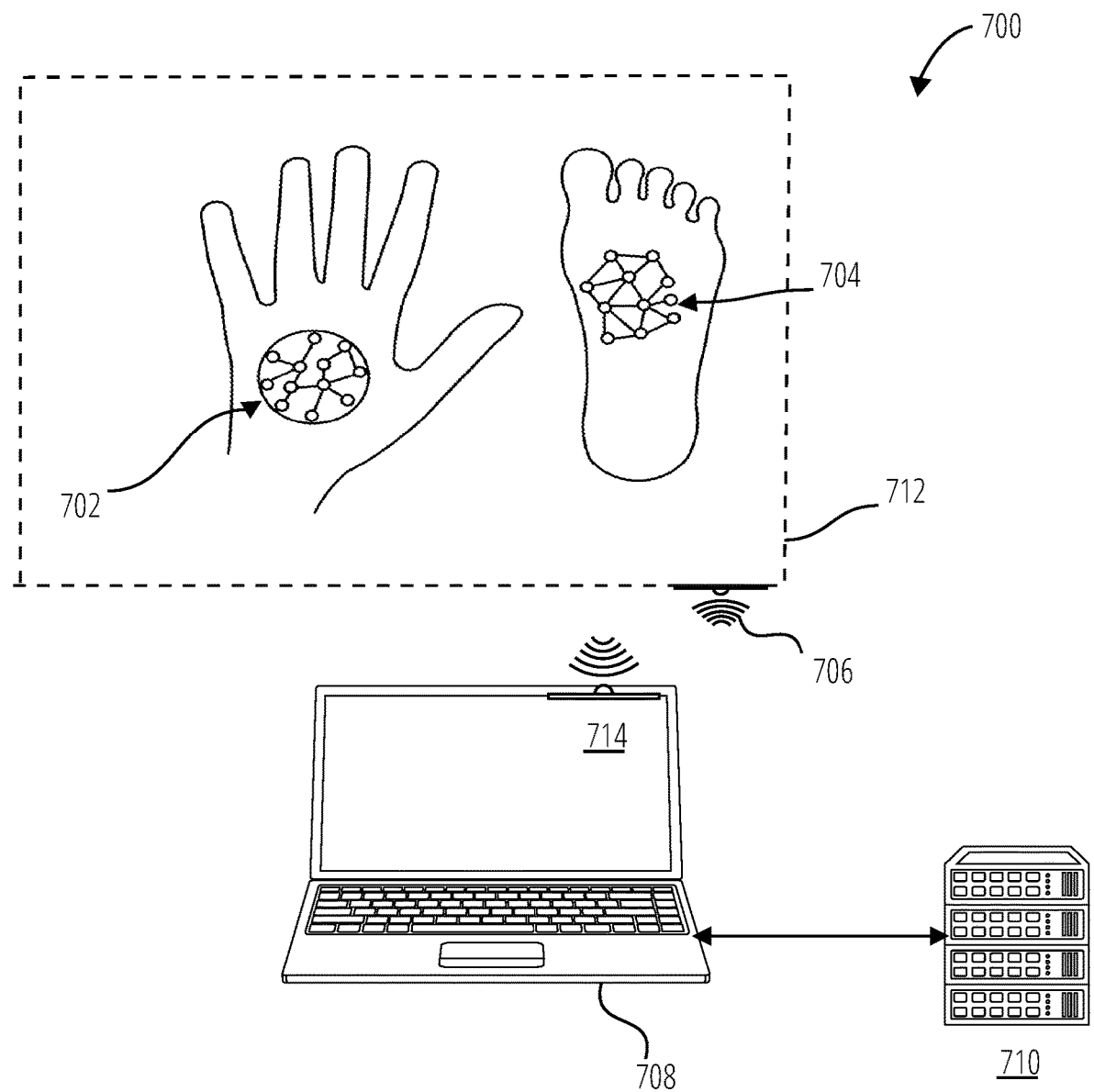
FIG. 7 illustrates a diagnostic system 700 a planar acceleration measurement and diagnostic system in accordance with one embodiment.

In the diagnostic system 700 embodiment of FIG. 7, the sensors 604 is disposed in a foot pad that adheres to the bottom of the foot (pedal arch deployment 704), specifically the pedal arch. The sensor is coupled with or includes an RF transmitter 706 (Bluetooth, WiFi, or other) connection to an RF receiver 714 of a display system 708 that displays real time waveforms and measures acceleration time pre, during, and post-surgical procedure. The display system 708 may communicate with a diagnostic system 710 that includes a diagnostic classifier such as exemplified by Table 900 in FIG. 9.

The sensors 604 may include an array of transducers (as illustrated) strategically positioned to measure acceleration in a network of blood vessels. A collection of readings may be made at each point in time from the sensor array, and collectively analyzed to identify pathologies in blood flow. The array of sensors may be positioned to align with key blood vessels for example, the illustrated blood vessels in the human foot 500 of FIG. 5.

In some embodiments, the sensors 604 may be arranged to align with the arteries of the deep palmar arch. This arch is a series of arteries formed at the junction of the ulnar and radial arteries in the palm of the hand. This semicircular artery branches into the fingers, where its divisions are known as palmar digital branches.

In another embodiment, the sensors 604 may be disposed in a pad placed on the technician's hand or as part of a glove (hand deployment 702) and engaged with the pedal arch by pressing the hand on the pedal arch, or engaged with the deep palmar arch by holding the patient's hand.

In yet another embodiment, the sensors 604 may be located in a non-weightbearing planar surface 712 upon which the patient can rest a foot or a hand.

Figure 8:
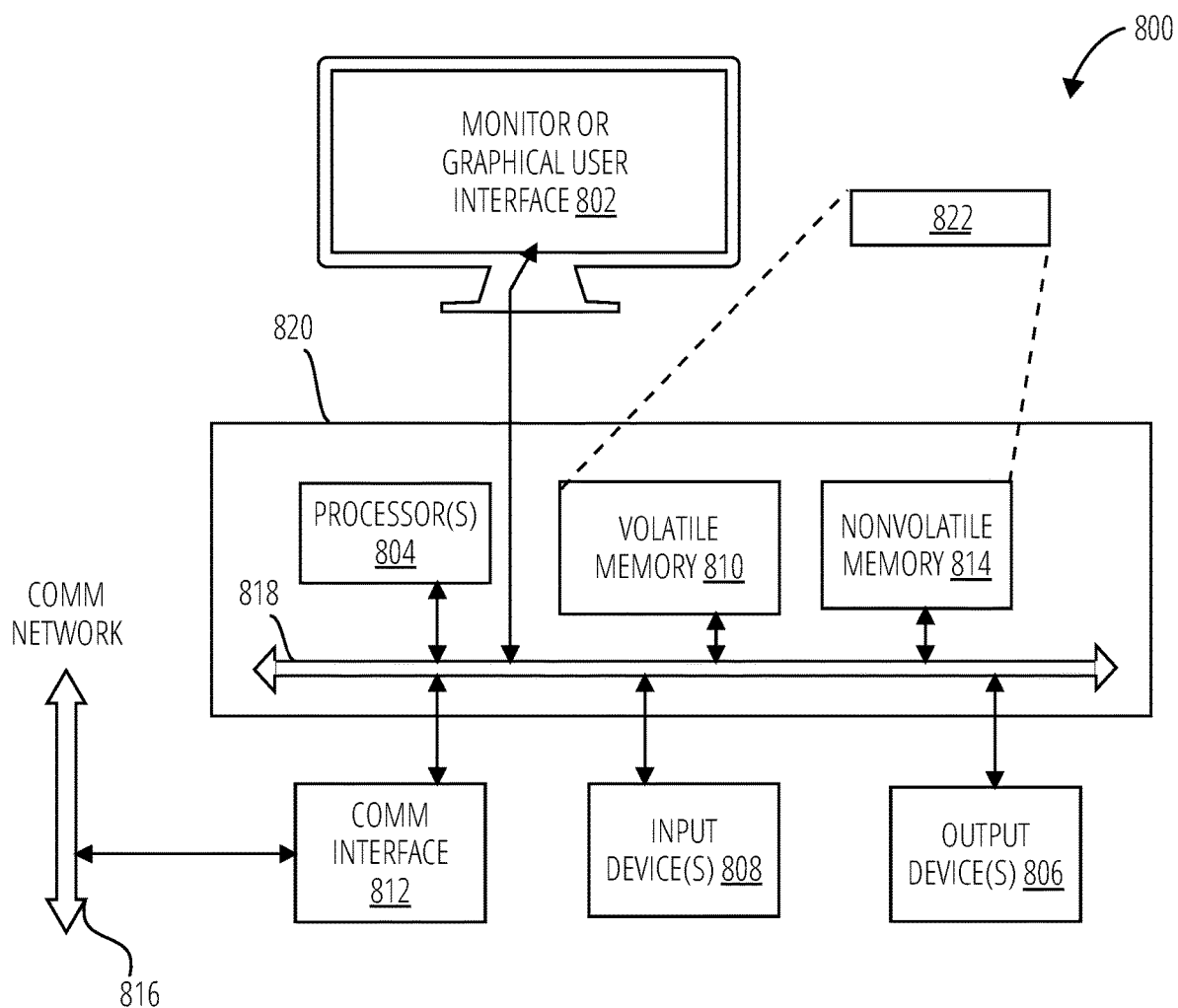
FIG. 8 is an example block diagram of a diagnostic system 800 that may incorporate embodiments of the present invention.

FIG. 8 is an example block diagram of a diagnostic system 800, such as display system 708 or diagnostic system 710, that may incorporate embodiments of the present invention. FIG. 8 is merely illustrative of a machine system to carry out aspects of the technical processes described herein, and does not limit the scope of the claims. One of ordinary skill in the art would recognize other variations, modifications, and alternatives. In one embodiment, the diagnostic system 800 typically includes a monitor or graphical user interface 802, a data processing system 820, a communication network interface 812, input device(s) 808, output device(s) 806, and the like.

As depicted in FIG. 8, the data processing system 820 may include one or more processor(s) 804 that communicate with a number of peripheral devices via a bus subsystem 818. These peripheral devices may include input device(s) 808, output device(s) 806, communication network interface 812, and a storage subsystem, such as a volatile memory 810 and a nonvolatile memory 814.

The volatile memory 810 and/or the nonvolatile memory 814 may store computer-executable instructions and thus forming logic 822 that when applied to and executed by the processor(s) 804 implement embodiments of the processes disclosed herein, such as measurement of blood flow acceleration in the pedal arch, and classifying an associated pathology.

The input device(s) 808 include devices and mechanisms for inputting information to the data processing system 820. These may include a keyboard, a keypad, a touch screen incorporated into the monitor or graphical user interface 802, audio input devices such as voice recognition systems, microphones, and other types of input devices. In various embodiments, the input device(s) 808 may be embodied as a computer mouse, a trackball, a track pad, a joystick, wireless remote, drawing tablet, voice command system, eye tracking system, and the like. The input device(s) 808 typically allow a user to select objects, icons, control areas, text and the like that appear on the monitor or graphical user interface 802 via a command such as a click of a button or the like.

The output device(s) 806 include devices and mechanisms for outputting information from the data processing system 820. These may include speakers, printers, infrared LEDs, and so on as well understood in the art.

The communication network interface 812 provides an interface to communication networks (e.g., communication network 816) and devices external to the data processing system 820. The communication network interface 812 may serve as an interface for receiving data from and transmitting data to other systems. Embodiments of the communication network interface 812 may include an Ethernet interface, a modem (telephone, satellite, cable, ISDN), (asynchronous) digital subscriber line (DSL), FireWire, USB, a wireless communication interface such as Bluetooth or Wi-Fi, a near field communication wireless interface, a cellular interface, and the like.

The communication network interface 812 may be coupled to the communication network 816 via an antenna, a cable, or the like. In some embodiments, the communication network interface 812 may be physically integrated on a circuit board of the data processing system 820, or in some cases may be implemented in software or firmware, such as "soft modems", or the like.

The diagnostic system 800 may include logic that enables communications over a network using protocols such as HTTP, TCP/IP, RTP/RTSP, IPX, UDP and the like.

The volatile memory 810 and the nonvolatile memory 814 are examples of tangible media configured to store computer readable data and instructions to implement various embodiments of the processes described herein. Other types of tangible media include removable memory (e.g., pluggable USB memory devices, mobile device SIM cards), optical storage media such as CD-ROMS, DVDs, semiconductor memories such as flash memories, non-transitory read-only-memories (ROMS), battery-backed volatile memories, networked storage devices, and the like. The volatile memory 810 and the nonvolatile memory 814 may be configured to store the basic programming and data constructs that provide the functionality of the disclosed processes and other embodiments thereof that fall within the scope of the present invention.

Logic 822 that implements embodiments of the present invention may be stored in the volatile memory 810 and/or the nonvolatile memory 814. Said software may be read from the volatile memory 810 and/or nonvolatile memory 814 and executed by the processor(s) 804. The volatile memory 810 and the nonvolatile memory 814 may also provide a repository for storing data used by the software.

The volatile memory 810 and the nonvolatile memory 814 may include a number of memories including a main random-access memory (RAM) for storage of instructions and data during program execution and a read only memory (ROM) in which read-only non-transitory instructions are stored. The volatile memory 810 and the nonvolatile memory 814 may include a file storage subsystem providing persistent (non-volatile) storage for program and data files. The volatile memory 810 and the nonvolatile memory 814 may include removable storage systems, such as removable flash memory.

The bus subsystem 818 provides a mechanism for enabling the various components and subsystems of data processing system 820 communicate with each other as intended. Although the communication network interface 812 is depicted schematically as a single bus, some embodiments of the bus subsystem 818 may utilize multiple distinct busses.

It will be readily apparent to one of ordinary skill in the art that the diagnostic system 800 may be a mobile device such as a smartphone, a desktop computer, a laptop computer, a rack-mounted computer system, a computer server, or a tablet computer device. As commonly known in the art, the diagnostic system 800 may be implemented as a collection of multiple networked computing devices. Further, the diagnostic system 800 will typically include operating system logic (not illustrated) the types and nature of which are well known in the art.

"Circuitry" in this context refers to electrical circuitry having at least one discrete electrical circuit, electrical circuitry having at least one integrated circuit, electrical circuitry having at least one application specific integrated circuit, circuitry forming a general purpose computing device configured by a computer program (e.g., a general purpose computer configured by a computer program which at least partially carries out processes or devices described herein, or a microprocessor configured by a computer program which at least partially carries out processes or devices described herein), circuitry forming a memory device (e.g., forms of random access memory), or circuitry forming a communications device (e.g., a modem, communications switch, or optical-electrical equipment).

"Firmware" in this context refers to software logic embodied as processor-executable instructions stored in read-only memories or media.

"Hardware" in this context refers to logic embodied as analog or digital circuitry.

"Logic" in this context refers to machine memory circuits, non-transitory machine readable media, and/or circuitry which by way of its material and/or material-energy configuration comprises control and/or procedural signals, and/ or settings and values (such as resistance, impedance, capacitance, inductance, current/voltage ratings, etc.), that may be applied to influence the operation of a device. Magnetic media, electronic circuits, electrical and optical memory (both volatile and nonvolatile), and firmware are examples of logic. Logic specifically excludes pure signals or software per se (however does not exclude machine memories comprising software and thereby forming configurations of matter).

"Programmable device" in this context refers to an integrated circuit designed to be configured and/or reconfigured after manufacturing. The term "programmable processor" is another name for a programmable device herein. Programmable devices may include programmable processors, such as field programmable gate arrays (FPGAs), configurable hardware logic (CHL), and/or any other type programmable devices. Configuration of the programmable device is generally specified using a computer code or data such as a hardware description language (HDL), such as for example Verilog, VHDL, or the like. A programmable device may include an array of programmable logic blocks and a hierarchy of reconfigurable interconnects that allow the programmable logic blocks to be coupled to each other according to the descriptions in the HDL code. Each of the programmable logic blocks may be configured to perform complex combinational functions, or merely simple logic gates, such as AND, and XOR logic blocks. In most FPGAs, logic blocks also include memory elements, which may be simple latches, flip-flops, hereinafter also referred to as "flops," or more complex blocks of memory. Depending on the length of the interconnections between different logic blocks, signals may arrive at input terminals of the logic blocks at different times.

"Software" in this context refers to logic implemented as processor-executable instructions in a machine memory (e.g. read/write volatile or nonvolatile memory or media).

Herein, references to "one embodiment" or "an embodiment" do not necessarily refer to the same embodiment, although they may. Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively, unless expressly limited to a single one or multiple ones. Additionally, the words "herein," "above," "below" and words of similar import, when used in this application, refer to this application as a whole and not to any particular portions of this application. When the claims use the word "or" in reference to a list of two or more items, that word covers all of the following interpretations of the word: any of the items in the list, all of the items in the list and any combination of the items in the list, unless expressly limited to one or the other. Any terms not expressly defined herein have their conventional meaning as commonly understood by those having skill in the relevant art(s).

Various logic functional operations described herein may be implemented in logic that is referred to using a noun or noun phrase reflecting said operation or function. For example, an association operation may be carried out by an "associator" or "correlator". Likewise, switching may be carried out by a "switch", selection by a "selector", and so on.

Those skilled in the art will recognize that it is common within the art to describe devices or processes in the fashion set forth herein, and thereafter use standard engineering practices to integrate such described devices or processes into larger systems. At least a portion of the devices or processes described herein can be integrated into a network processing system via a reasonable amount of experimentation. Various embodiments are described herein and presented by way of example and not limitation.

Those having skill in the art will appreciate that there are various logic implementations by which processes and/or systems described herein can be effected (e.g., hardware, software, or firmware), and that the preferred vehicle will vary with the context in which the processes are deployed. If an implementer determines that speed and accuracy are paramount, the implementer may opt for a hardware or firmware implementation; alternatively, if flexibility is paramount, the implementer may opt for a solely software implementation; or, yet again alternatively, the implementer may opt for some combination of hardware, software, or firmware. Hence, there are numerous possible implementations by which the processes described herein may be effected, none of which is inherently superior to the other in that any vehicle to be utilized is a choice dependent upon the context in which the implementation will be deployed and the specific concerns (e.g., speed, flexibility, or predictability) of the implementer, any of which may vary. Those skilled in the art will recognize that optical aspects of implementations may involve optically-oriented hardware, software, and or firmware.

Those skilled in the art will appreciate that logic may be distributed throughout one or more devices, and/or may be comprised of combinations memory, media, processing circuits and controllers, other circuits, and so on. Therefore, in the interest of clarity and correctness logic may not always be distinctly illustrated in drawings of devices and systems, although it is inherently present therein. The techniques and procedures described herein may be implemented via logic distributed in one or more computing devices. The particular distribution and choice of logic will vary according to implementation.

What is claimed is:

1. A diagnostic system for performing pedal Doppler ultrasound measurements, the system comprising:
    a sensor mount;
    a plurality of ultrasound sensors disposed in the sensor mount, the plurality of ultrasound sensors adapted to contact, but not penetrate skin;
    the plurality of ultrasound sensors spatially separated from one another and adapted in an arrangement to permit alignment of the ultrasound sensors with a plurality of blood vessels of a pedal arch when the sensor mount is contacted with the foot, such that each ultrasound sensor is aligned with a respective blood vessel of the pedal arch selected from a group consisting of a posterior tibial artery, an anterior tibial artery, a peroneal artery, a lateral tarsal artery, a dorsalis pedis artery, an arcuate artery, a deep plantar artery, a lateral plantar artery, and a medial plantar artery, thereby facilitating the measurement of ultrasound signals from the plurality of blood vessels of the pedal arch; and
    control and processing circuitry connectable to said plurality of ultrasound sensors for:
    controlling the plurality of ultrasound sensors to emit ultrasound energy, detect ultrasound signals received from the plurality of blood vessels, such that a collection of ultrasound readings are obtained at a given point in time, each reading corresponding to each ultrasound sensor aligned with the respective blood vessel of the pedal arch selected from the group; and
    collectively analyzing the detected ultrasound signals received from the plurality of blood vessels to obtain a measure characterizing blood flow within the plurality of blood vessels of the pedal arch at the given point in time.

2. The diagnostic system of claim 1, wherein the sensor mount includes a pad.

3. The diagnostic system of claim 1, wherein the sensor mount is non-weightbearing.

4. The diagnostic system of claim 1, wherein the sensor mount includes a pad that is configured to be placed on a technician's hand that is engaged with the pedal arch.

5. The diagnostic system according to claim 1 wherein the sensor mount comprises a glove that is wearable by a clinician, thereby permitting alignment of each of the ultrasound sensors with the respective blood vessels of the plurality of blood vessels of the pedal arch of a subject when the glove is contacted with the pedal arch of the subject.

6. A method comprising:
    arranging a plurality of ultrasound sensors in contact with a pedal arch, wherein the plurality of ultrasound sensors are disposed in a sensor mount and are spatially separated from one another, such that each ultrasound sensor is adapted to target a different vessel of the pedal arch;
    aligning the plurality of ultrasound sensors in the sensor mount with blood vessels of the pedal arch, such that each ultrasound sensor is aligned with a respective blood vessel of the pedal arch, thereby facilitating the measurement of ultrasound signals from the plurality of blood vessels of the pedal arch;
    controlling the plurality of ultrasound sensors to emit ultrasound energy, detect ultrasound signals received from the plurality of blood vessels such that a collection of ultrasound readings are obtained at a given point in time, each reading corresponding to each ultrasound sensor aligned with the respective blood vessel of the pedal arch; and
    collectively analyzing the detected ultrasound signals received from the plurality of blood vessels to obtain a measure characterizing blood flow within the plurality of blood vessels of the pedal arch at the given point in time.

7. The method of claim 6, wherein the sensor mount includes a pad, the method further comprising engaging, by a technician's hand, the pad with the pedal arch.

8. The method according to claim 6 wherein the sensor mount comprises a glove that is wearable by a clinician, wherein each of the ultrasound sensors are aligned with the respective plurality of blood vessels of the pedal arch of a subject when the glove is contacted with the pedal arch of the subject.

* * * * *